(12) United States Patent
Yu et al.

(10) Patent No.: US 11,417,190 B1
(45) Date of Patent: Aug. 16, 2022

(54) FOOT WEARING DEVICE FOR CORRECTING SITTING POSTURE AND METHOD FOR CORRECTING SITTING POSTURE

(71) Applicant: Chaobin Yu, Fujian (CN)

(72) Inventors: Chaobin Yu, Fujian (CN); Xingtong Yu, Fujian (CN); Zhenyuan Yu, Fujian (CN)

( * ) Notice: Subject to any disclaimer, the term of this patent is extended or adjusted under 35 U.S.C. 154(b) by 0 days.

(21) Appl. No.: 17/485,477

(22) Filed: Sep. 26, 2021

(30) Foreign Application Priority Data

Aug. 13, 2021 (CN) .......................... 202110932372.8

(51) Int. Cl.
*G08B 21/04* (2006.01)
*G08B 7/06* (2006.01)

(52) U.S. Cl.
CPC ........... *G08B 21/0446* (2013.01); *G08B 7/06* (2013.01)

(58) Field of Classification Search
None
See application file for complete search history.

(56) References Cited

U.S. PATENT DOCUMENTS

| 5,928,227 A * | 7/1999 | Howard, III | A61B 18/00 341/176 |
| 2008/0204223 A1* | 8/2008 | Chu | G01S 11/14 340/539.13 |
| 2017/0087411 A1* | 3/2017 | Bender | A63B 24/0062 |

* cited by examiner

*Primary Examiner* — John F Mortell

(57) ABSTRACT

A foot wearing device includes a left wearing unit, configured to be worn on a left foot of a user; a right wearing unit, configured to be worn on a right foot of the user; a signal transmitting unit, arranged on one of a left side of the left wearing unit and a right side of the right wearing unit and configured to transmit signals; a signal detecting unit, arranged on the other of the left side of the left wearing unit and the right side of the right wearing unit and configured to detect signals transmitted by the signal transmitting unit; and a prompt unit, electrically connected to the signal detecting unit and configured to prompt the user if the signal detecting unit detects that there are signals transmitted by the signal transmitting unit.

17 Claims, 10 Drawing Sheets

FOOT WEARING DEVICE FOR CORRECTING SITTING POSTURE AND METHOD FOR CORRECTING SITTING POSTURE

CROSS-REFERENCE TO RELATED APPLICATIONS

The application claims priority of Chinese patent application 2021109323728, filed on 13, Aug. 2021, which is incorporated herein by reference in its entireties.

FIELD

The subject natter herein generally relates to correcting posture, and particularly relates to a foot wearing device for correcting sitting posture and a method for correcting, sitting posture.

BACKGROUND

As the saying goes, "sit like a clock and stand like a pine." Correct sitting posture can not only effectively improve people's external mental state, but also keep people healthy and effectively reduce problems such as low back pain.

There are many kinds of bad sitting posture, such as bowing your head, bending your body, crossing your legs, etc. Many people have a bad habit of crossing their legs. This sitting posture is easy to bend down and hunch when sitting, resulting in uneven pressure distribution of lumbar spine and thoracic spine. In the long run, it is bound to compress spinal nerves and cause lower back pain. Moreover, it will hinder blood circulation of legs and cause varicose veins in the legs. In severe cases, there are often poor venous reflux, sudden blue tendons, ulcers, phlebitis, bleeding and other diseases.

SUMMARY

In order to correct the bad sitting posture of the crossed legs, the present disclosure provides a foot wearing device and a method for correcting the sitting posture, which can effectively prompt the user, correct the sitting posture in time and effectively protect the user's health.

A foot wearing device includes:
a left wearing unit, configured to be worn on a left foot of a user;
a right wearing unit, configured to be worn on a right foot of the user;
a signal transmitting unit, arranged on one of a left side of the left wearing unit and a right side of the right wearing unit and configured to transmit signals;
a signal detecting unit, arranged on the other of the left side of the left wearing unit and the right side of the right wearing unit and configured to detect signals transmitted by the signal transmitting unit; and
a prompt unit, electrically connected to the signal detecting unit and configured to prompt the user if the signal detecting unit detects that there are signals transmitted by the signal transmitting unit.

In at least one embodiment, the foot wearing device further includes a first timing switch electrically connected between the signal detecting unit and the prompt unit, wherein the first timing switch configured to time a time interval t1 between two adjacent times when the signal detecting unit detects signals transmitted by the signal transmitting unit and configured to switch on/off a connection between the signal detecting unit and the prompt unit based on the time interval t1.

In at least one embodiment, if the time interval t1 is less than a predetermined value T1, the first timing switch switches on the connection between the signal detecting unit and the prompt unit and the prompt unit prompt the user to correct sitting posture.

In at least one embodiment, the predetermined value T1 is 1 second.

In at least one embodiment, the foot wearing device further includes a second timing switch electrically connected between the signal detecting unit and the prompt unit, wherein the second timing switch configured to time a signal duration t2 when the signal detecting unit detects signals transmitted by the signal transmitting unit and configured to switch on/off a connection between the signal detecting unit, and the prompt unit based on the signal duration t2.

In at least one embodiment, if the signal duration t2 is greater than a predetermined value T2, the second timing switch switches on the connection between the signal detecting unit and the prompt unit and the prompt unit prompt the user to correct sitting posture.

In at least one embodiment, the predetermined value T2 is 2 seconds.

In at least one embodiment, the foot wearing device further includes a shielding unit configured to form a shielding space tween the signal transmitting unit and the signal detecting unit when the right wearing unit is on, a right side of the left wearing unit.

In at least one embodiment, the shielding unit is arranged at a right side of the left wearing unit and/or a left side of the right wearing unit.

In at least one embodiment, a signal transmitting angle along which the signal transmitting unit transmits signals is 120 degrees to 180 degrees.

In at least one embodiment, the signal transmitting unit is a photoelectric signal transmitter, and the signal detecting unit is a photoelectric signal detector.

In at least one embodiment, the prompt unit is one or more of a buzzer, a horn, a light prompt, a vibration device, and a graphene heating device.

In at least one embodiment, the foot wearing device further includes a power unit. The power unit comprises a left power part arranged at the left wearing unit and a right power part arranged at the right wearing unit.

In at least one embodiment, each of the left power part and the right power part is a chargeable battery.

A method, for correcting sitting posture includes:
provide a foot wearing device, the foot wearing device includes:
  left wearing unit, configured to be worn on a left foot of a user;
  a right wearing unit, configured to be worn on a right foot of the user;
  a signal transmitting unit, arranged on one of a left side of the left wearing unit and a right side of the right wearing unit and configured to transmit signals
  a signal detecting unit, arranged, on the other of the left side of the left wearing unit and the right side of the right wearing unit and configured to detect signals transmitted by the signal transmitting unit; and
  a prompt unit, electrically connected to the signal detecting unit and configured to prompt the user if the signal detecting unit detects that there are signals transmitted by the signal transmitting unit;
wear the left wearing unit on a user's left foot and wear the right wearing unit on the user's right foot;

detect by the signal detecting unit whether there are signals transmitted by the signal transmitting unit; and prompt the user by the prompt unit to correct sitting posture if there are signals transmitted by the signal transmitting unit.

In at least one embodiment, the foot wearing device further includes a first timing switch connected between the signal detecting unit and the prompt unit, the method further includes: time by the first timing switch a time interval t1 between two adjacent, times when the signal detecting unit detects signals transmitted by the signal transmitting unit; switch on a connection between the signal detecting unit and the prompt unit if the time interval t1 is less than a predetermined value T1, and switch off the connection between the signal detecting unit and the prompt unit if the time interval t1 is not less than a predetermined value T1.

In at least one embodiment the foot wearing device further includes a second timing switch connected between the signal detecting unit and the prompt unit, the method further includes: time by the second timing switch a signal duration t2 when the signal detecting unit detects signals transmitted by the signal transmitting unit; switch on a connection between the signal detecting unit and the prompt unit if the signal duration t2 is greater than a predetermined value T2; prompt the user by the prompt unit to correct sitting posture; and switch off the connection between the signal detecting unit and the prompt unit if the signal duration t2 is not greater than a predetermined value T2.

In at least one embodiment, the foot wearing device further includes a first timing, switch connected between the signal detecting unit and the prompt unit and a second timing switch connected between the signal detecting unit and the prompt unit, the method further includes: time by the first timing switch a time interval t1 between two adjacent times when the signal detecting unit detects signals transmitted by the signal transmitting unit; switch on a connection between the signal detecting unit and the prompt unit if the time interval t1 is less than a predetermined value T1; prompt the user by the prompt unit to correct sitting posture; time by the second timing switch a signal duration t2 when the signal detecting unit detects signals transmitted by the signal transmitting unit, if the time interval t1 is not less than a predetermined value T1, switch on a connection between the signal detecting unit and the prompt unit if the signal duration t2 is greater than a predetermined value T2; prompt the user by the prompt unit to correct sitting posture; and switch off the connection between, the signal detecting unit and the prompt unit if the signal duration t2 is not greater than a predetermined value T2.

In at least one embodiment, after the step of prompt the user by the prompt unit to correct sitting posture, the method further includes: detect by the detecting unit whether there are signals transmitted by the signal transmitting unit; and prompt the user by the prompt unit to correct sitting, posture if there are signals transmitted by the signal transmitting unit.

Through the foot wearing device, when the left wearing unit and the right wearing unit are respectively put on the user's left foot and right foot, the signal transmitting unit transmits signals towards the left side of the left wearing unit or towards the right side of the right wearing unit. If the user crosses his feet, for example, crossing legs, the signal detecting unit corresponds to the signal transmitting unit to receive the signals transmitted by the signal transmitting unit, the prompt unit prompts the user to correct sitting posture, which can effectively reduce bad sitting posture and protect the user's health.

BRIEF DESCRIPTION OF THE DRAWINGS

Implementations of the present disclosure will now be described, by way of embodiment, with reference to the attached figures. It should be understood, the drawings are shown for illustrative purpose only, for ordinary person skilled in the art, other drawings obtained from these drawings without paying creative labor by an ordinary person skilled in the art should be within scope of the present disclosure.

DETAILED DESCRIPTION

Figure 1:
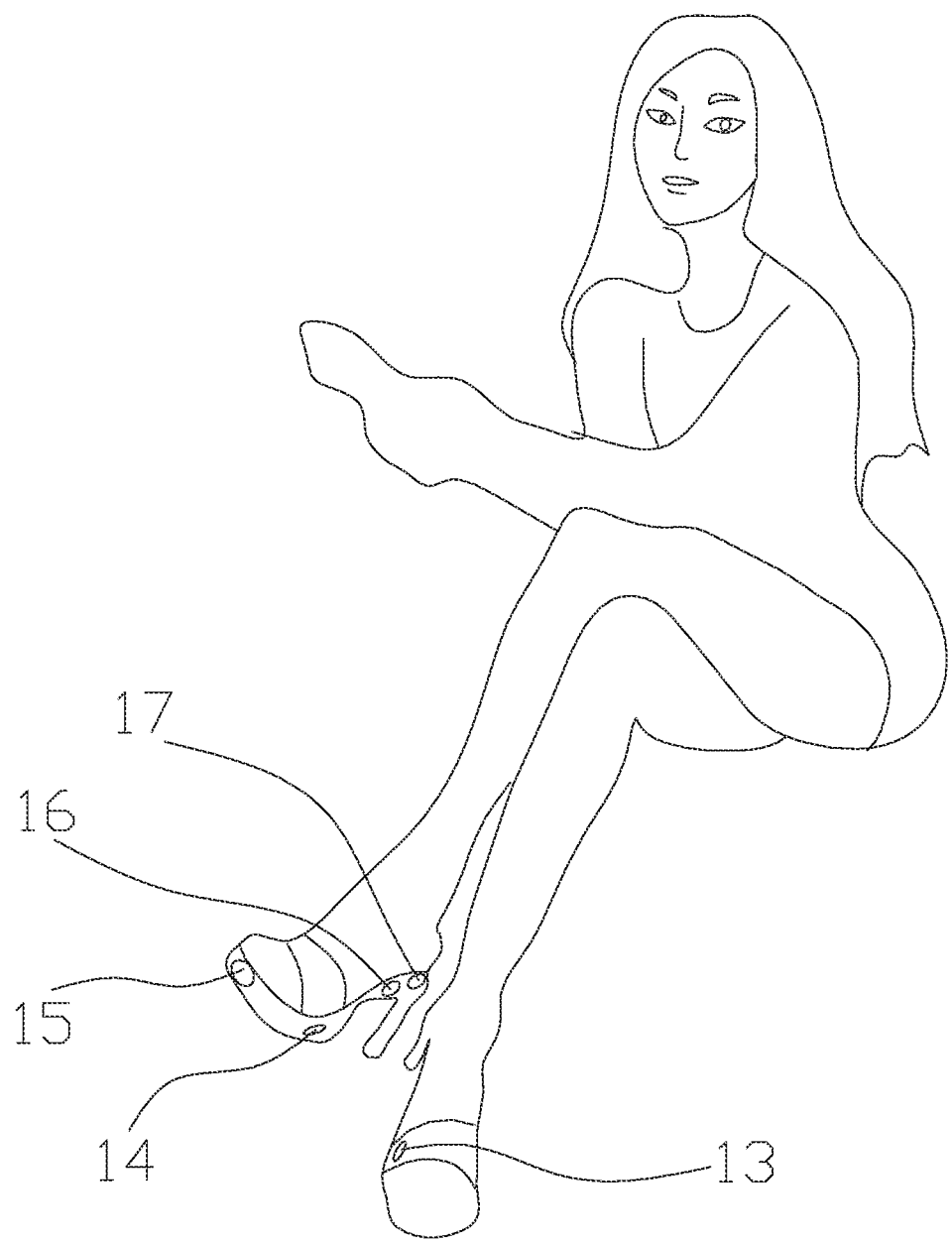
FIG. 1 is a schematic view of a foot wearing device in a use state according to a first embodiment of the present disclosure.
Figure 2:
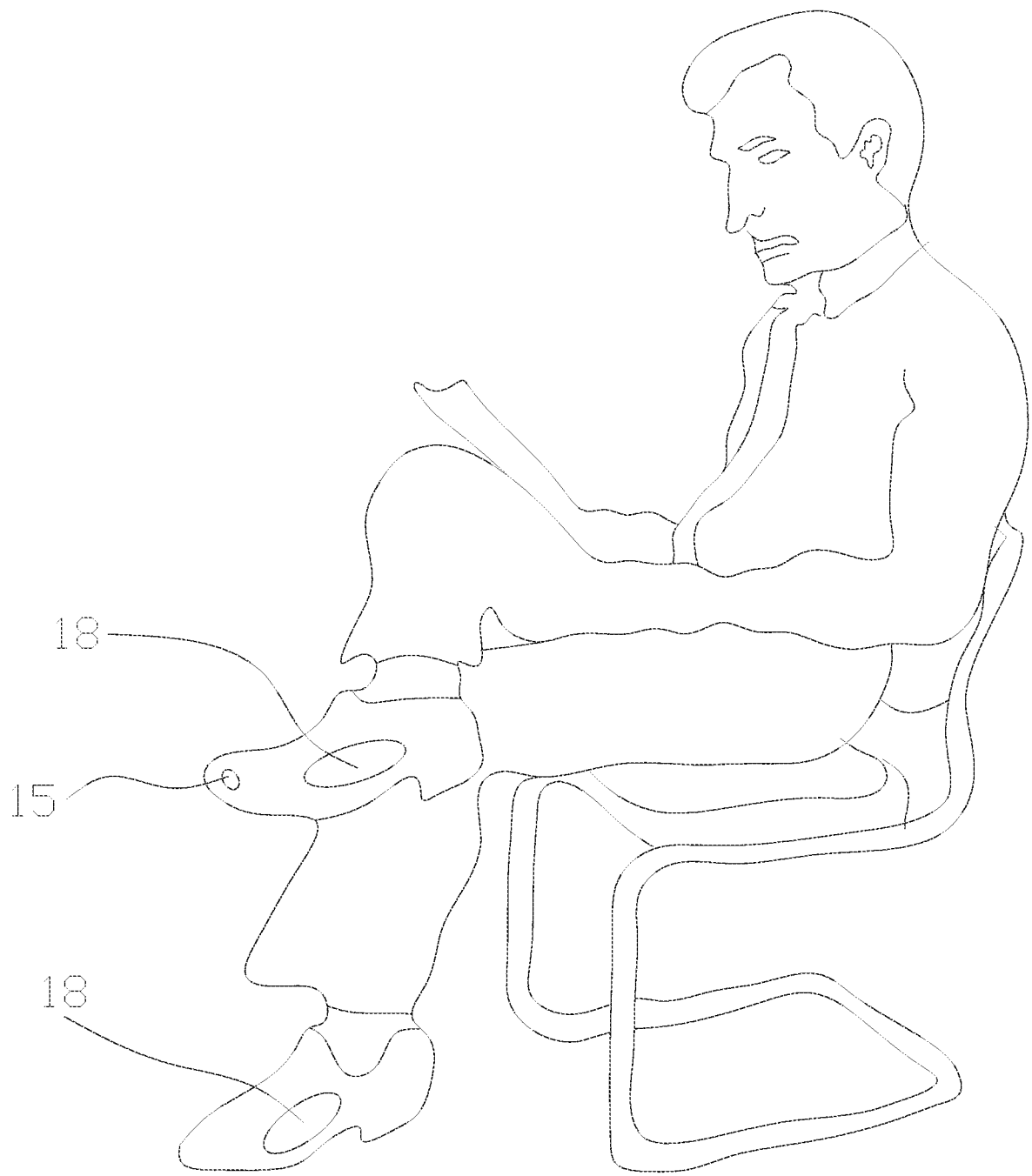
FIG. 2 is a schematic view of a foot wearing device in a use state according to a second embodiment of the present disclosure.
Figure 3:
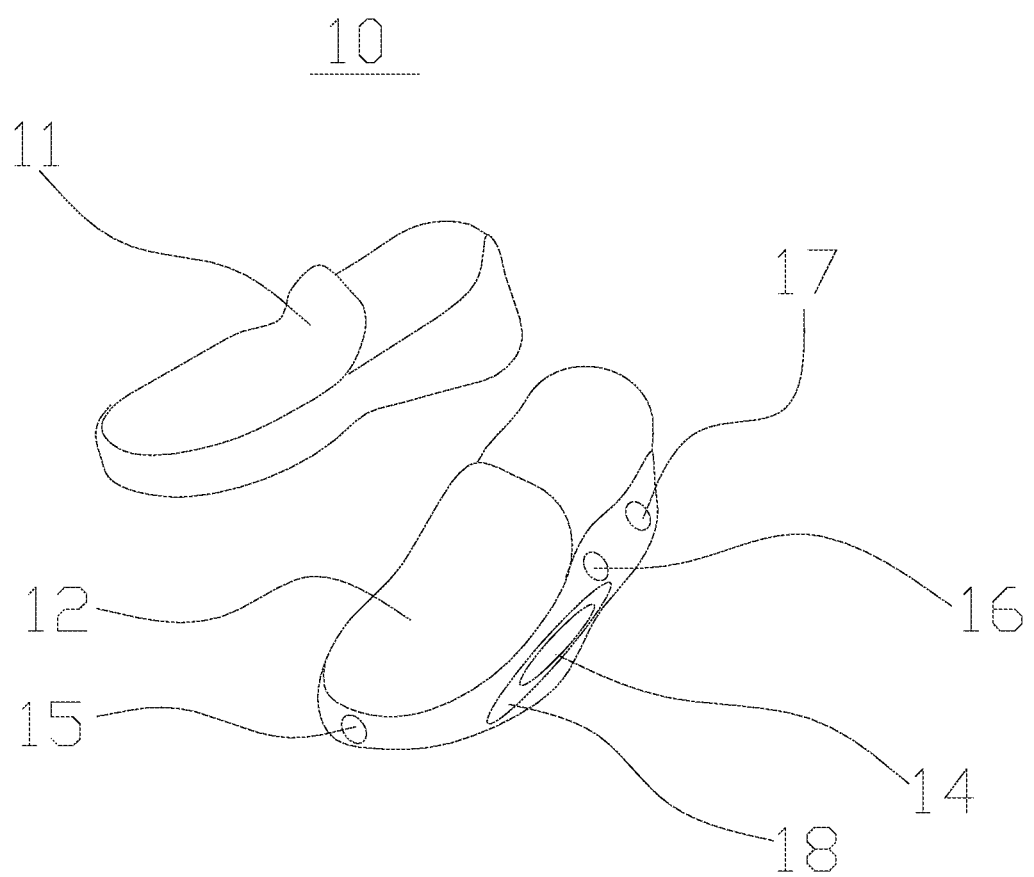
FIG. 3 is a schematic view of a foot wearing device according to a third embodiment of the present disclosure.
Figure 4:
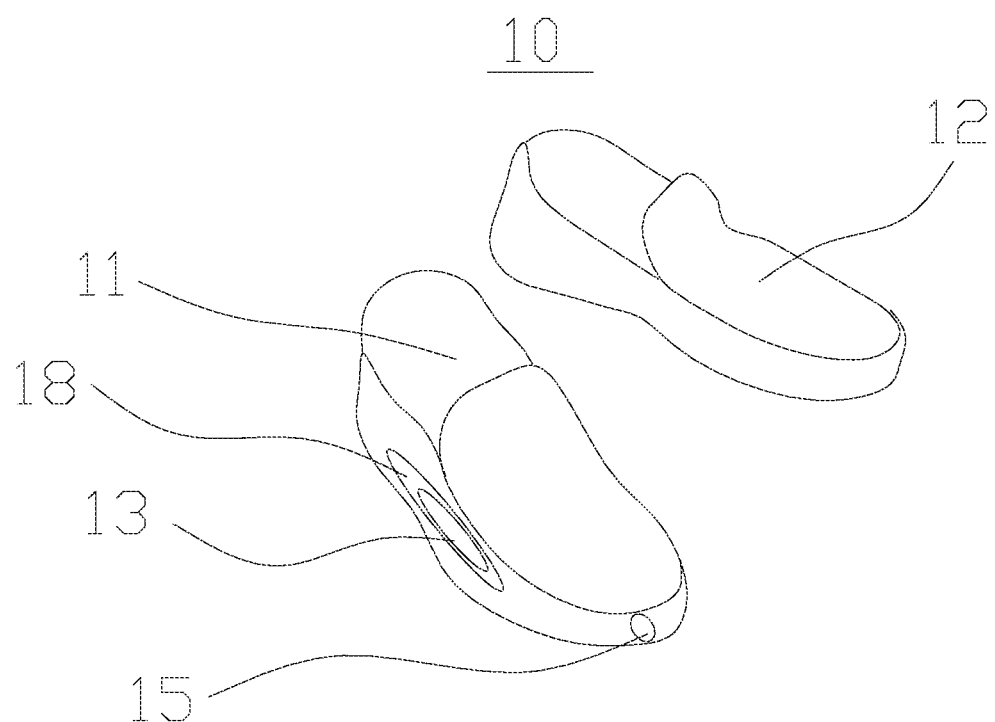
FIG. 4 is a schematic view of the foot wearing device of FIG. 3 from another view.
Figure 5:
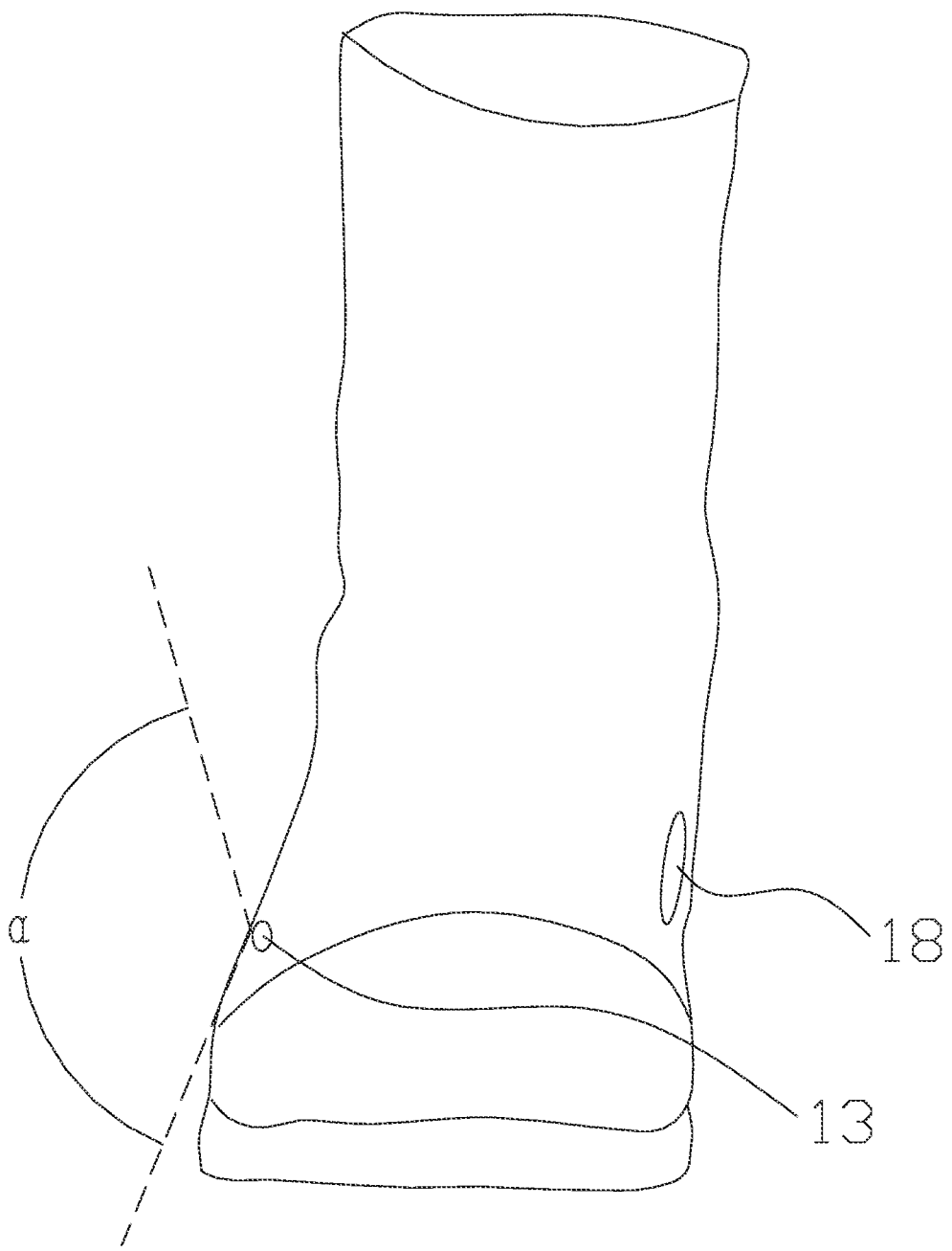
FIG. 5 shows a schematic diagram of a signal transmittal angle in which the signal transmitting unit transmits signals.
Figure 6:
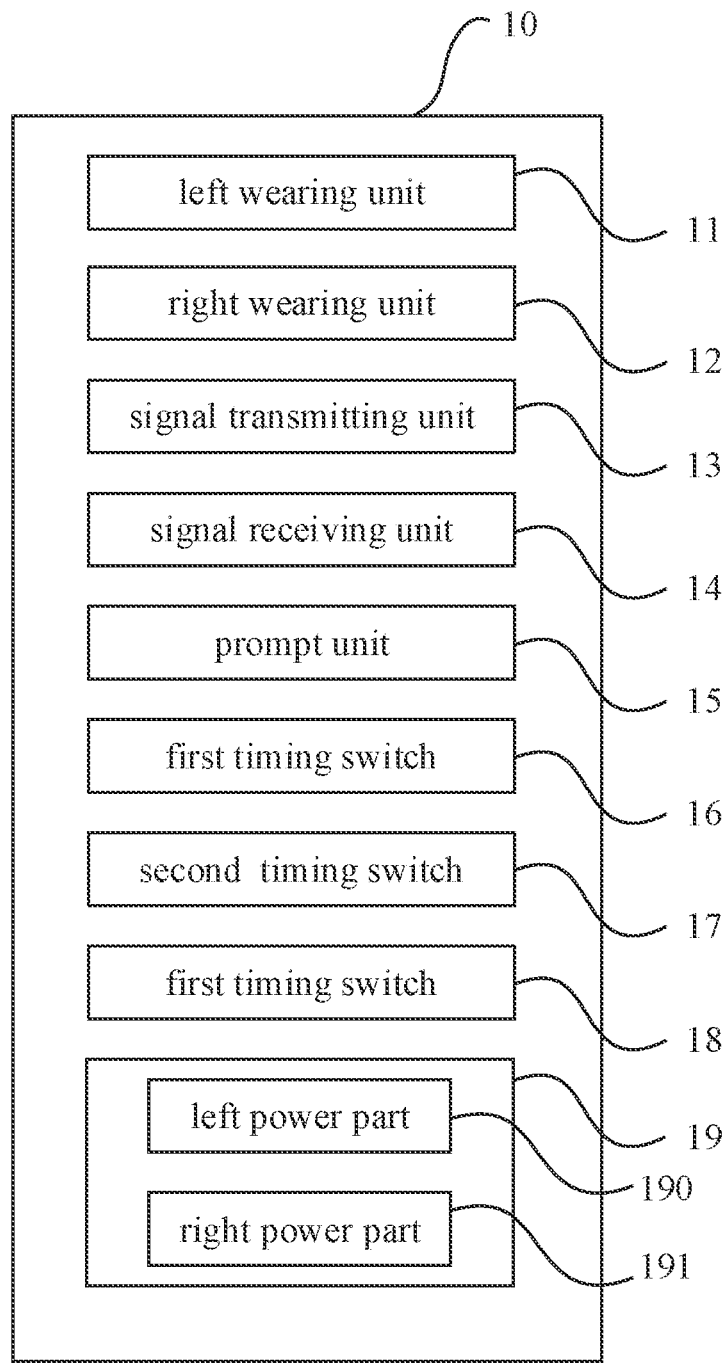
FIG. 6 is a block diagram of a foot wearing device according to an embodiment of the present disclosure.

It will be appreciated that for simplicity and clarity of illustration, where appropriate, reference numerals have been repeated among the different figures to indicate corresponding or analogous elements. In addition, numerous specific details are set forth in order to provide a thorough understanding of the exemplary embodiments described herein. However, it will be understood by those of ordinary skill in the art that the exemplary embodiments described herein may be practiced without these specific details. In other instances, methods, procedures, and components have not been described in detail so as not to obscure the related relevant feature being described. Also, the description is not to be considered as limiting the scope of the exemplary embodiments described herein. The drawings are not necessarily to scale and the proportions of certain parts may be exaggerated to better illustrate details and features of the present disclosure.

The term "comprising" when utilized, means "including, but not necessarily limited to"; it specifically indicates open-ended inclusion or membership in the so-described combination, group, series, and the like. The disclosure is illustrated by way of example and not by way of limitation in the figures of the accompanying drawings in which like references indicate similar elements. It should be noted that references to "an" or "one" embodiment in this disclosure are not necessarily to the same embodiment, and such references can mean "at least one". In addition, the terms "first" and "second" are used for descriptive purposes only and cannot be understood as indicating or implying relative importance or implying the number of indicated technical features. Thus, the features defined as "first" and "second" may explicitly or implicitly include one or more of the said features. In the description of embodiments of the invention, "a plurality of" means two or more, unless otherwise specifically defined.

Referring to FIGS. 1-6 FIG. 1 shows a foot wearing device. The foot wearing device 10 includes a left wearing unit 11 configured to wear on a left foot of a user and a-right wearing unit 12 configured to wear on a right foot of the user, a signal transmitting unit 13 arranged on a left side of the left wearing unit 11 or on a right side of the right wearing unit 12 and configured to send signals, a signal detecting unit arranged on the right side of the right wearing unit 12 or on the left side of the left wearing unit 11 and configured to detect signals sent by the signal transmitting unit 13, and a prompt unit 15 electrically connected to the signal detecting unit 14 and configured to prompt the user when the signal detecting unit 14 receives signals sent by the signal transmitting unit 13.

The signal transmitting unit 13 and the signal detecting unit 14 are arranged at the left wearing unit and the right wearing unit respectively. A direction in which the signal transmitting unit transmits the signal is towards the left side of the left wearing unit 11 or the right side of the right wearing unit 12. When the left foot and right foot of the user cross each other, such as crossing two legs, the signal detecting unit 14 corresponds to the signal transmitting unit 13 and can receive the signal transmitted by the signal transmitting unit 13. At this time, the prompt unit 15 can prompt the user to correct bad sitting posture in time. The foot wearing device has simple structure and reasonable design, which can effectively avoid adverse consequences such as scoliosis caused by the user's wrong sitting posture.

In at least one embodiment, the foot wearing device further includes a first timing switch 16 electrically connected to the signal detecting unit 14 and the prompt unit 15. The first timing switch 16 is configured to time the time interval t1 between two adjacent times when the signal detecting unit 14 receives the signal transmitted by the signal transmitting unit 13 and configured to switch on/off a connection between the prompt unit 15 and the signal detecting unit 14. Through the first timing switch 16, the time interval t1 is obtained and based on the time interval t1, it can be determined that whether the user cross the left and right foot frequently, for example, crossing legs and shaking the legs quickly. At this time, if the time interval t1 is less than a predetermined value T1, the first timing switch 16 switches the prompt unit 15 to be connected to the signal detecting unit 14. The prompt unit 15 prompts the user to correct sitting posture in time. Therefore, the foot wearing device can effectively determine whether the user is in error sitting posture and prompt the user to correct error sitting posture in time, which effectively prevent the user from suffering chronic disease due to error sitting posture. In detail, the predetermined interval T1 can be 1s. If the user crosses foot once, the signal detecting unit 14 receives the signal transmitted by the signal transmitting unit 13 for the first time. If the user crosses foot again, the signal detecting unit 14 receives the signal transmitted by the signal transmitting unit 13 for the second time. The time interval between the first time and the second time is the interval t1. If t1 is less than T1 (such as 1s), the first timing switch 16 switches on the connection between the signal detecting unit 14 and the prompt unit 15 so that the prompt unit 15 can prompt the user to correct sitting posture in time, thereby effectively protecting user's health.

In at least one embodiment, the foot wearing device further includes a second timing switch 17 configured to time signal duration t2 when the signal detecting unit 14 receives the signal transmitted by the signal transmitting unit 13 and configured to switch on/off the connection between the prompt unit 15 and the signal detecting unit 14. Through the second timing switch 17, the signal duration t2 is obtained and based on the signal duration t2, it can be determined that whether the user cross the left foot and right foot for a long time, for example, keeping crossing legs for a long time. At this time, if the signal duration t2 is less than a predetermined value T2, the second timing switch 17 switches the prompt unit 15 to be connected to the signal detecting unit 14. The prompt unit 15 prompt the user to correct sitting posture in time. Therefore, the foot wearing device can effectively determine whether the user is in error sitting posture and prompt the user to correct error sitting posture in time, which effectively prevent the user from suffering chronic disease due to error sitting posture. In detail, the predetermined interval T2 can be 2s. If the user cross foot, the signal detecting unit 14 receives the signal transmitted by the signal transmitting unit 13 for the first time. When the time period during which the signal detecting unit 14 keeps receiving the signal transmitted by the signal transmitting unit 13 is up to T2 (such as 2s), the second timing switch 17 switches on the connection between the signal detecting unit 14 and the prompt unit 15 so that the prompt unit 15 can prompt the user to correct sitting posture in time, thereby effectively protecting user's health.

In at least one embodiment, the left wearing unit 11 or the right wearing unit 12 is provided with a shielding unit 18. The shielding unit 18 can be arranged on a side of the signal transmitting unit 13 adjacent to the signal detecting unit 14 or on a side of the signal detecting unit 14 adjacent to the signal transmitting, unit 13. The shielding unit 18 is configured to form a shielding space between the left wearing unit 11 and the right wearing unit 12 when the right wearing unit 12 is located on the right side of the left wearing unit 11. Through such arrangement, when the right wearing unit 12 is located on the right side of the left wearing unit 11, that is, when the user's feet are in a normal position, the shielding unit 18 is located between the left wearing unit 11 and the right wearing unit 12. The shielding unit 18 can shield the signal transmission between the signal transmitting unit 13 and the signal detecting unit 14, prevent the signal detecting unit 14 from erroneously receiving the signal transmitted by the signal transmitting unit 13 to prevent false trigger, thereby improving reliability of the foot wearing device. Therefore, the foot wearing device can effectively detect the user's wrong sitting posture and prompt the user to correct it in time. The structure is simple and reliable.

In at least one embodiment, a signal transmitting angle at in which the signal transmitting unit 13 transmits signals is 120 degrees to 180 degrees so that the signal transmitted by the signal transmitting unit 13 can cover the left side of the left wearing unit 11 or the right side of the right wearing unit 12 as possible. Through such arrangement, it is beneficial for the signal detecting unit 14 effectively receiving the signals transmitted by the signal transmitting unit 13. Because there are many ways to cross legs, the signal transmitting angle $\alpha$ is large enough to effectively ensure that the signal detecting unit 14 can detect the signal, so as to improve the practicability of the foot wearing device and effectively protect the user's health.

In at least one embodiment, the signal transmitting unit 13 can be a photoelectric signal transmitter, and the signal detecting unit 14 can be a photoelectric signal detector. The photoelectric signal transmitter cooperating with the photoelectric signal detector can detect signals accurately and quickly, thereby, effectively detecting the user's sitting posture and protect the user's health.

In at least one embodiment, the signal transmitting unit 13, the signal detecting unit 14, the prompt unit 15, the first timing switch 16 and the second timing switch 17 are detachably connected at the left wearing unit 11 or the right wearing unit 12. Detachable connection is convenient for replacing, cleaning and maintenance of the signal transmitting unit 13, the signal detecting unit 14, the prompt unit 15, the first timing switch 16 and the second timing switch 17, which can effectively reduce cost, prolong service life of the foot wearing device. Therefore, the foot wearing device can continuously and effectively detect user's sitting posture and prompt the user to correct sitting posture in time.

In at least one embodiment, the foot wearing device further includes a power unit 19. Each of the signal transmitting unit 13, the signal detecting unit 14, the prompt unit 15, the first timing switch 16 and the second timing switch 17 is electrically connected to the power unit 19. The power unit 19 can provide energy for the foot wearing device to improve endurance of the foot wearing device, thereby enabling the foot wearing device to continuously protect the user's health.

In at least one embodiment, the power unit 19 can include two power parts configured to provide energy for the first wearing unit 11 and the second wearing unit 12 respectively. The two power parts can include a left power part 190 arranged at the first wearing unit 11 and a right power part 191 arranged at the second wearing unit 12 respectively.

In at least one embodiment, each of the first wearing unit 11 and a right power part 191 can be a chargeable battery. Rechargeable batteries are energy-saving and environment-friendly, and can also improve endurance of products, which is simple and efficient.

In at least one embodiment, the prompt unit 15 can be one or more of buzzer, horn, light prompt, vibration device, graphene heating device, etc. for example, a separate buzzer can prompt the user through sound signal, and the combination of centralized prompt signals can prompt the user more comprehensively and effectively, prevent the user from missing prompt information, and ensure that the user can correct the sitting posture in time.

Figure 7:
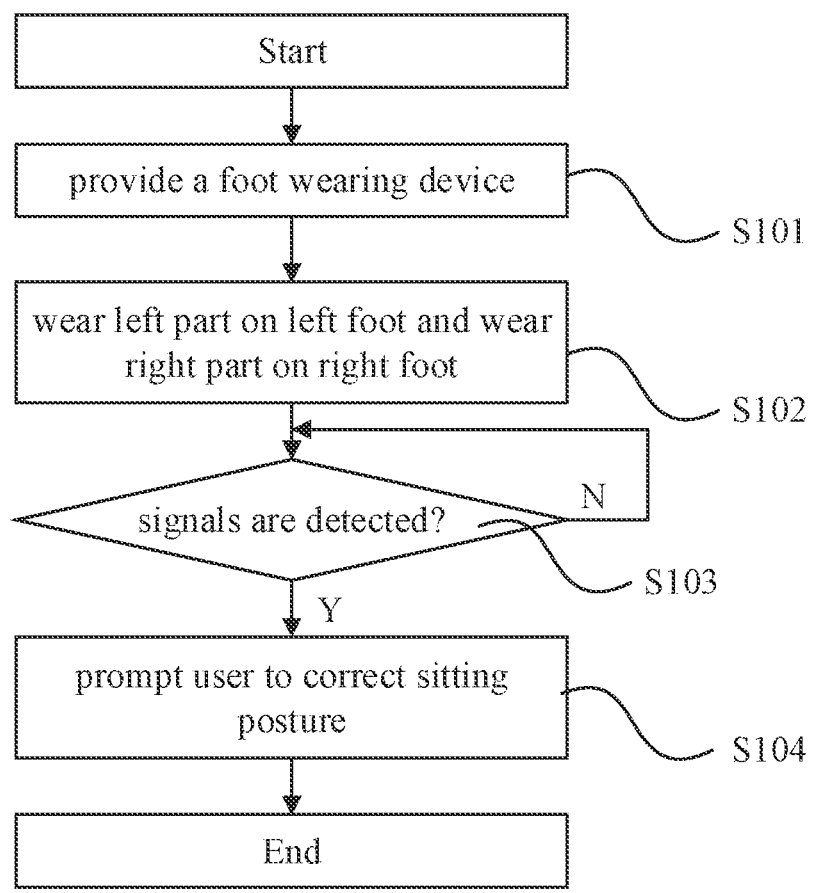
FIG. 7 is an exemplary flow chart of a method for correcting sitting posture according to a fourth embodiment of the present disclosure.

Referring to FIG. 7, a method for correcting sitting posture provided by a fourth embodiment of the present disclosure includes following steps.

Step S101, provide a foot wearing device 10. The foot wearing device includes a left wearing unit 11 configured to wear on a left foot of a user and a right wearing unit 12 configured to wear on a right foot of the user, a signal transmitting unit 13 arranged on a left side of the left wearing unit 11 or on a right side of the right wearing unit 12 and configured to send signals, a signal detecting unit arranged on the right side of the right wearing unit 12 or on the left side of the left wearing unit 11 and configured to detect signals sent by the signal transmitting unit 13, and a prompt unit 15 electrically connected to the signal detecting unit 14 and configured to prompt the user when the signal detecting unit 14 receives signals sent by the signal transmitting unit 13.

Step S102, wear the left wearing unit 11 on the user's left foot and wear the right wearing unit 12 on the user's right foot.

Step S103, the signal detecting unit 14 detects whether there are signals transmitted by the signal transmitting unit 13.

Step S104, the prompt unit 15 prompts the user to correct sitting posture if the signal detecting unit 14 receives the signals transmitted by the signal transmitting unit 13.

Through the foot wearing device, when the left wearing unit 11 and the right wearing unit 12 are respectively put on the user's left foot and right foot, the signal transmitting unit 13 transmits signals towards the left side of the left wearing unit or towards the right side of the right wearing unit. If the user crosses his feet, for example, crossing legs, the signal detecting unit 14 corresponds to the signal transmitting unit 13 to receive the signals transmitted by the signal transmitting unit 13, the prompt unit 15 prompts the user to correct sitting posture, which can effectively reduce bad sitting posture and protect the user's health.

Figure 8:
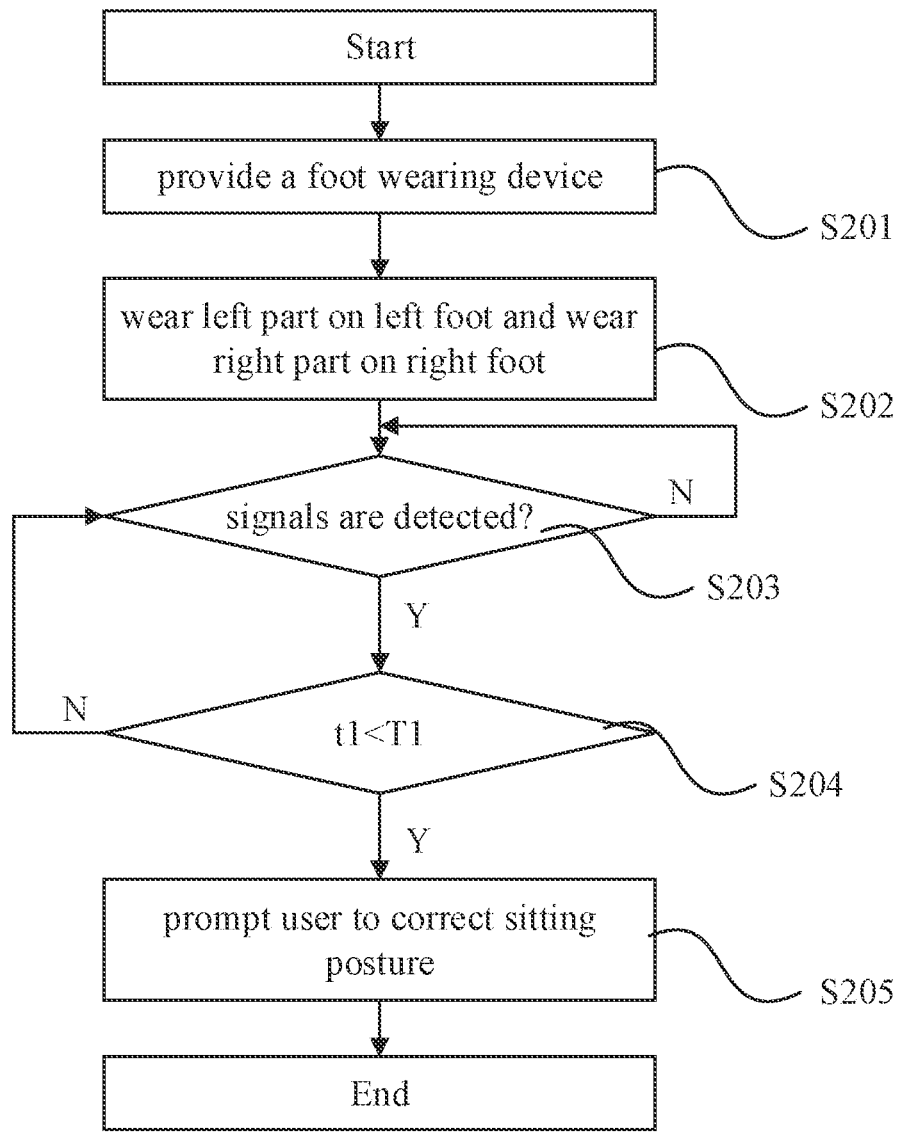
FIG. 8 is an exemplary flow chart of a method for correcting sitting posture according to a fifth embodiment of the present disclosure.

Referring to FIG. 8, a method for correcting sitting posture provided by a fifth embodiment of the present disclosure includes following steps.

Step S201, Step S101, provide a foot wearing device 10. The foot wearing device includes a left wearing unit 11 configured to wear on a left foot of a user and a right wearing unit 12 configured to wear on a right foot of the user, a signal transmitting unit 13 arranged on a left side of the left wearing unit 11 or on a right side of the right wearing unit 12 and configured to send signals, a signal detecting unit arranged on the right side of the right wearing unit 12 or on the left side of the left wearing unit 11 and configured to detect signals sent by the signal transmitting emit 13, and a prompt unit 15 electrically connected to the signal detecting unit 14 and configured to prompt the user when the signal detecting unit 14 receives signals sent by the signal transmitting unit 13.

Step S202, wear the left wearing unit 11 on the user's left foot and wear the right wearing unit 12 on the user's right foot.

Step S203, the signal detecting unit 14 detects whether there are signals transmitted by the signal transmitting unit 13.

In at least one embodiment, the foot wearing device 10 further includes a first timing switch 16, the signal detecting unit 14 and the prompt unit 15 are electrically connected to the first timing switch 16. In Step S204, the first timing switch times a time interval t1 between two adjacent times when the signal detecting unit 14 detects the signal transmitted by the signal transmitting unit 13, switches on the connection between the signal detecting unit 14 and the prompt unit 15 if t1 is less than a predetermined value T1; and switches off the connection between the signal detecting unit 14 and the prompt unit 15 if t1 is not less than the predetermined value T1.

Through the first timing switch 16, the time interval t1 is obtained and based on the time interval t1, it can be determined that whether the user cross the left and right foot frequently, for example, crossing legs and shaking the legs quickly. At this time, if the time interval t1 is less than a predetermined value T1, the first timing switch 16 switches the prompt unit 15 to be connected to the signal detecting unit 14. The prompt unit 15 prompts the user to correct sitting posture in time. Therefore, the foot wearing device can effectively determine whether the user is in error sitting posture and prompt the user to correct error sitting posture in time, which effectively prevent the user from suffering chronic disease due to error sitting posture and protect the user's health.

Step S205, if the time interval t1 is less than the predetermined value T1, the first timing switch 16 switches on the connection between the signal detecting unit 14 and the prompt unit 15 and the prompt unit 15 prompts the user to correct sitting posture.

Through the foot wearing device, when the left wearing unit 11 and the right wearing unit 12 are respectively put on the user's left foot and right foot, the signal transmitting unit 13 transmits signals towards the left side of the left wearing unit or towards the right side of the right wearing unit. If the user crosses his feet, for example, crossing legs, the signal detecting unit 14 corresponds to the signal transmitting unit 13 to receive the signals transmitted by the signal transmitting unit 13, the prompt unit 15 prompts the user to correct sitting posture, which can effectively reduce bad sitting posture and protect the user's health. In detail, the predetermined interval T1 can be 1s. If the user crosses foot once, the signal detecting unit 14 receives the signal transmitted by the signal transmitting unit 13 for the first time. If the user crosses foot again, the signal detecting unit 14 receives the signal transmitted by the signal transmitting unit 13 for the second time. The time interval between the first time and the second time is the interval t1. If t1 is less than T1 (such as 1s), the first timing switch 16 switches on the connection between, the signal detecting unit 14 and the prompt unit 15 so that the prompt unit 15 can prompt the user to correct sitting posture in time, thereby effectively protecting user's health.

Figure 9:
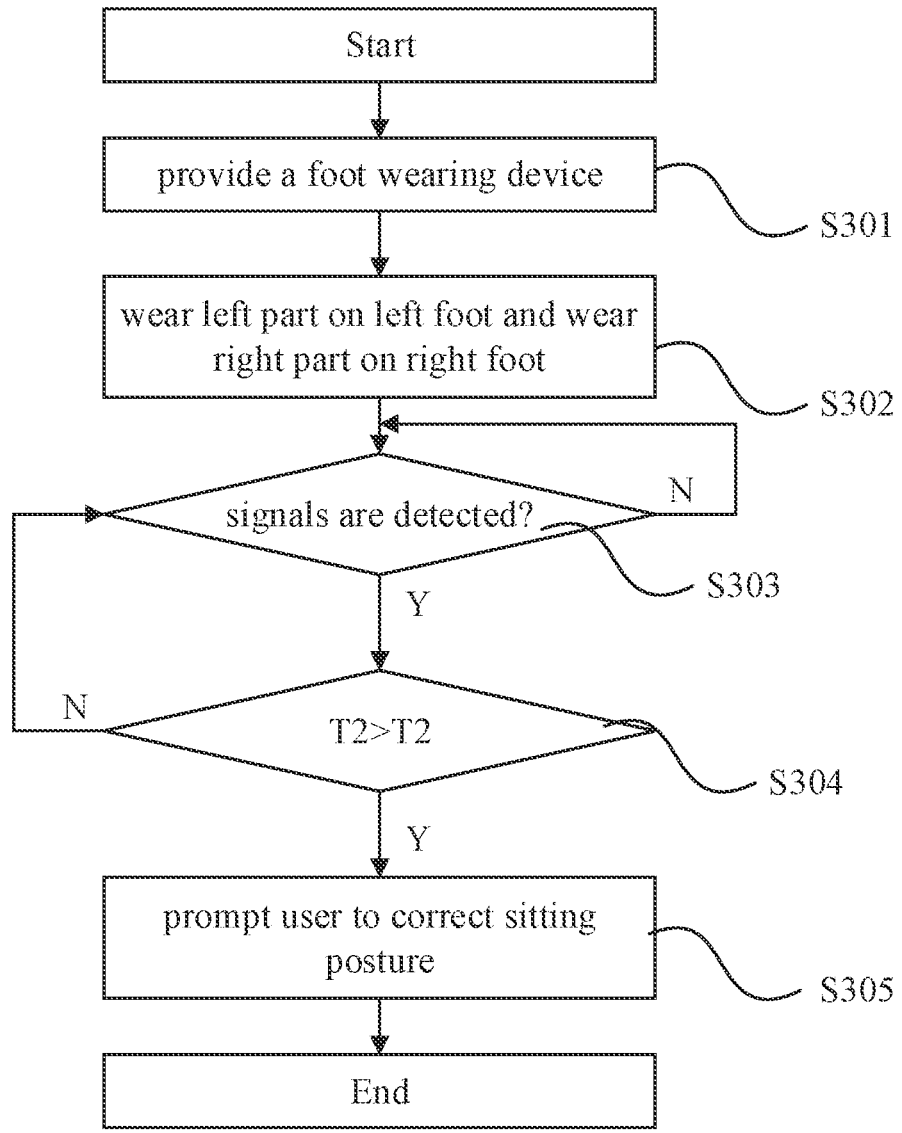
FIG. 9 is an exemplary flow chart of a method for correcting sitting posture according to a sixth embodiment of the present disclosure.

Referring to FIG. 9, a method for correcting sitting posture provided by a sixth embodiment of the present disclosure includes following steps.

Step S301, provide a foot wearing device 10. The foot wearing device includes a left wearing unit 11 configured to wear on a left foot of a user and a right wearing unit 12 configured to wear on a right foot of the user, a signal transmitting unit 13 arranged on a left side of the left wearing unit 11 or on a right side of the right wearing unit 12 and configured to send signals, a signal detecting unit arranged on the right side of the right wearing unit 12 or on the left side of the left wearing unit 11 and configured to detect signals sent by the signal transmitting unit 13, and a prompt unit 15 electrically connected to the signal detecting unit 14 and configured to prompt the user when the signal detecting unit 14 receives signals sent by the signal transmitting unit 13.

Step S302, wear the left wearing unit 11 on the user's left foot and wear the right wearing unit 12 on the user's right foot.

Step S303, the signal detecting unit 14 detects whether there are signals transmitted by the signal transmitting unit 13.

In at least one embodiment, the foot wearing device 10 further includes a second timing switch 17, the signal detecting unit 14 and the prompt unit 15 are electrically connected to the second timing switch 17. In Step S304, the second timing switch 17 times a signal duration t2 when the signal detecting unit 14 detects the signal transmitted by the signal transmitting unit 13, switches on the connection between the prompt unit 15 and the signal detecting unit 14 if the signal duration t2 is greater than a predetermined value T2; and switches off the connection between the prompt unit 15 and the signal detecting unit 14 if the signal duration t2 is not greater than the predetermined value T2.

Through the second timing switch 17, the signal duration t2 is obtained and based on the signal duration t2, it can be determined that whether the user cross the left foot and right foot for a long time, for example, keeping crossing legs for a long time. At this time, if the signal duration t2 is less than a predetermined value T2, the second timing switch 17 switches the prompt unit 15 to be connected to the signal detecting unit 14. The prompt unit 15 prompt the user to correct sitting posture in time. Therefore, the foot wearing device can effectively determine whether the user is in error sitting posture and prompt the user to correct error sitting posture in time, which effectively prevent the user from suffering chronic disease due to error sitting posture.

Step S305, the second timing switch 17 switches on the connection between the prompt unit 15 and the signal detecting unit 14 if the signal duration t2 is greater than a predetermined value T2, and the prompt unit 15 prompts the user to correct sitting posture.

Through the foot wearing device, when the left wearing unit 11 and the right wearing unit 12 are respectively put on the user's left foot and right foot, the signal transmitting unit 13 transmits signals towards the left side of the left wearing unit or towards the right side of the right wearing unit. If the user crosses his feet, for example, crossing legs, the signal detecting unit 14 corresponds to the signal transmitting unit 13 to receive the signals transmitted by the signal transmitting unit 13, the prompt unit 15 prompts the user to correct sitting posture, which can effectively reduce bad sitting posture and protect the user's health. In detail, the predetermined interval T2 can be 2s. If the user cross foot, the signal detecting unit 14 receives the signal transmitted by the signal transmitting unit 13 for the first time. When the time period during which the signal detecting unit 14 keeps receiving the signal transmitted by the signal transmitting unit 13 is up to T2 (such as 2s), the second timing switch 17 switches on the connection between the signal detecting unit 14 and the prompt unit 15 so that the prompt unit 15 can prompt the user to correct sitting posture in time, thereby effectively protecting user's health.

Figure 10:
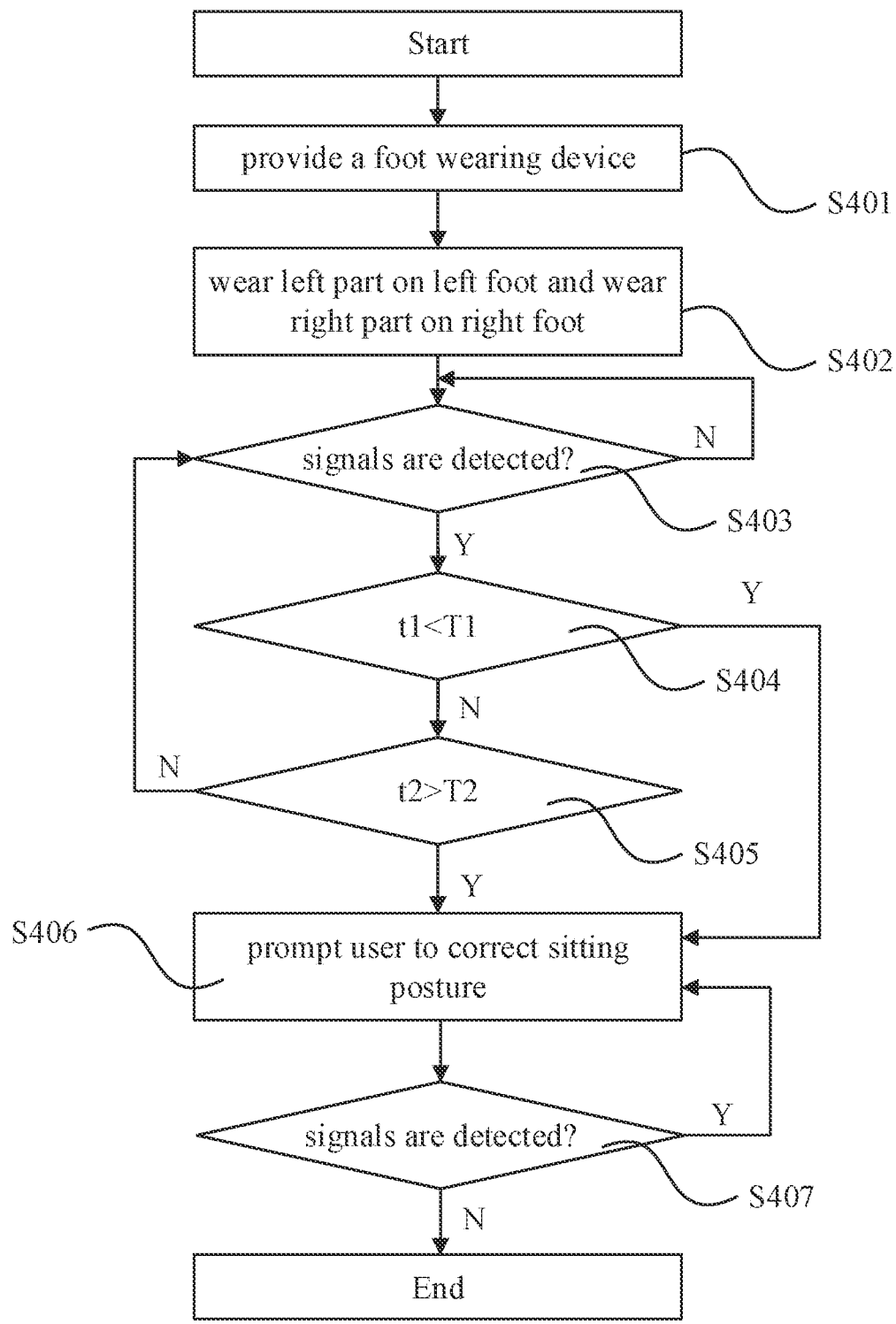
FIG. 10 is an exemplary flow chart of a method for correcting sitting posture according to a seventh embodiment of the present disclosure.

Referring to FIG. 10, a method for correcting sitting posture provided by a seventh embodiment of the present disclosure includes following steps.

Step S401, provide a foot wearing device 10. The foot wearing device includes a left wearing unit 11 configured to wear on a left foot of a user and a right wearing unit 12 configured to wear on a right foot of the user, a signal transmitting unit 13 arranged on a left side of the left wearing unit 11 or on a right side of the right wearing unit 12 and configured to send signals, a signal detecting unit arranged on the right, side of the right wearing unit 12 or on the left side of the left wearing unit 11 and configured to detect signals sent by the signal transmitting unit 13, and a prompt unit 15 electrically connected to the signal detecting unit 14 and configured to prompt the user when the signal detecting unit 14 receives signals sent by the signal transmitting unit 13.

Step S402, wear the left wearing unit 11 on the user's left foot and wear the right wearing unit 12 on the user's right foot.

Step S403, the signal detecting unit 14 detects whether there are signals transmitted by the signal transmitting unit 13.

In at least one embodiment, the foot wearing device 10 further includes a first timing switch 16, the signal detecting unit 14 and the prompt unit 15 are electrically connected to the first timing switch 16.

Step S404, the first timing switch times a time interval t1 between two adjacent times when the signal detecting unit 14 detects the signal transmitted by the signal transmitting unit 13, switches on the connection between the signal detecting unit 14 and the prompt unit 15 if t1 is less than a predetermined value T1; and switches off the connection between the signal detecting unit 14 and the prompt unit 15 if t1 is not less than the predetermined value T1.

Through the first timing switch 16, the time interval t1 is obtained and based on the time interval t1, it can be determined that whether the user cross the left and right foot frequently, for example, crossing legs and shaking the legs quickly. At this time, if the time interval t1 is less than, a predetermined value T1, the first timing switch 16 switches the prompt unit 15 to be connected to the signal detecting unit 14. The prompt unit 15 prompts the user to correct sitting posture in time. Therefore, the foot wearing device can effectively determine whether the user is in error sitting posture and prompt the user to correct error sitting posture in time, which effectively prevent the user from suffering chronic disease due to error sitting posture and protect the user's health. In detail, the predetermined interval T1 can be 1s. If the user crosses foot once, the signal detecting unit 14 receives the signal transmitted by the signal transmitting unit 13 for the first time. If the user crosses foot again, the signal detecting unit 14 receives the signal transmitted by the signal transmitting unit 13 for the second time. The time interval between the first time and the second time is the interval t1. If t1 is less than T1 (such as 1s), the first timing switch 16 switches on the connection between the signal detecting unit 14 and the prompt unit 15 so that the prompt unit 15 can prompt the user to correct sitting posture in time, thereby effectively protecting user's health.

In at least one embodiment, the foot wearing device 10 further includes a second timing switch 17, the signal detecting unit 14 and the prompt unit 15 are electrically connected to the second timing switch 17.

In Step S405, the second timing switch 17 times a signal duration t2 when the signal detecting unit 14 detects the signal transmitted by the signal transmitting unit 13 if t1 is not less than T1, switches on the connection between the prompt unit 15 and the signal detecting unit 14 if the signal duration t2 is greater than a predetermined value T2; and switches off the connection between the prompt unit 15 and the signal detecting unit 14 if the signal duration t2 is not greater than the predetermined value T2.

Through the second timing switch 17, the signal duration t2 is obtained and based on the signal duration t2, it can be determined that, whether the user cross the left foot and right foot for a long time, for example, keeping crossing legs for a long time. At this time, if the signal duration t2 is less than a predetermined value T2, the second timing switch 17 switches the prompt unit 15 to be connected to the signal detecting unit 14. The prompt unit 15 prompt the user to correct sitting posture in time. Therefore, the foot wearing device can effectively determine whether the user is in error sitting posture and prompt the user to correct error sitting posture in time, which effectively prevent the user from suffering chronic disease due to error sitting posture and protect the user's health. In detail, the predetermined interval T2 can be 2s. If the user cross foot, the signal detecting unit 14 receives the signal transmitted b the signal transmitting unit 13 for the first time. When the time period during which the signal detecting unit 14 keeps receiving the signal transmitted by the signal transmitting unit 13 is up to T2 (such as 2s), the second timing switch 17 switches on the connection between the signal detecting unit 14 and the prompt unit 15 so that the prompt unit 15 can prompt the user to correct sitting posture in time, thereby effectively protecting user's health.

Step S406, the connection between the signal detecting unit 14 and the prompt unit 15 is switched on and the prompt unit 15 prompts the user to correct sitting posture, if t1 is less than T1 or t2 is greater than T2.

Through the foot wearing device, when the left wearing unit 11 and the right wearing unit 12 are respectively put on the user's left foot and right foot, the signal transmitting unit 13 transmits signals towards the left side of the left wearing unit or towards the right side of the right wearing unit. If the user crosses his feet, for example, crossing legs, the signal detecting unit 14 corresponds to the signal transmitting unit 13 to receive the signals transmitted by the signal transmitting unit 13, the prompt unit 15 prompts the user to correct sitting posture, which can effectively reduce bad sitting posture and protect the user's health.

Step S407, the signal detecting unit 14 detects whether there are signals transmitted by the signal transmitting unit 13. The process goes back to Step S406 if there are signals transmitted by the signal transmitting unit 13.

Through step S407, the signal detecting unit 14 can further determine whether the user has corrected sitting posture after being prompted at Step S406. If the user has not corrected sitting posture, the signal detecting unit 14 will detect that there are still signals transmitted by the signal transmitting unit 13. At this time, the prompt unit 15 will prompt the user again to correct sitting posture in time. The prompt unit 15 will keep prompting the user until the user corrects sitting posture. Therefore, it is beneficial for ensuring the user in correct sitting posture, thereby protecting the user's health.

The above description only describes embodiments of the present disclosure, and is not intended to limit the present disclosure, various modifications and changes can be made to the present disclosure. Any modifications, equivalent substitutions, improvements, etc. made within the spirit and scope of the present disclosure are intended to be included within the scope of the present disclosure.

What is claimed is:

1. A foot wearing device, comprising:
  a left wearing unit, configured to be worn on a left foot of a user;
  a right wearing unit, configured to be worn on a right foot of the user;
  a signal transmitting unit, arranged on one of a left side of the left wearing unit and a right side of the right wearing unit and configured to transmit signals;
  a signal detecting unit, arranged on the other of the left side of the left wearing unit and the right side of the right wearing unit and configured to detect signals transmitted by the signal transmitting unit; and
  a prompt unit, electrically connected to the signal detecting unit and configured to prompt the user if the signal detecting unit detects that there are signals transmitted by the signal transmitting unit; and
  a first timing switch electrically connected between the signal detecting unit and the prompt unit, wherein the first timing switch configured to time a time interval t1 between two adjacent times when the signal detecting unit detects signals transmitted by the signal transmitting unit and configured to switch on/off a connection between the signal detecting unit and the prompt unit based on the time interval t1;
  if the time interval t1 is less than a predetermined value T1, the first timing switch switches on the connection between the signal detecting unit and the prompt unit and the prompt unit prompt the user to correct sitting posture.

2. The foot wearing device according to claim 1, wherein the predetermined value T1 is 1 second.

3. The foot wearing device according to claim 1, further comprising a second timing switch electrically connected between the signal detecting unit and the prompt unit, wherein the second timing switch configured to time a signal duration t2 when the signal detecting unit detects signals transmitted by the signal transmitting unit and configured to switch on/off a connection between the signal detecting unit and the prompt unit based on the signal duration t2.

4. The foot wearing device according to claim 3, wherein if the signal duration t2 is greater than a predetermined value T2, the second timing switch switches on the connection between the signal detecting unit and the prompt unit and the prompt unit prompt the user to correct sitting posture.

5. The foot wearing device according to claim 4, wherein the predetermined value T2 is 2 seconds.

6. The foot wearing device according to claim 1, further comprising a shielding unit configured to form a shielding space tween the signal transmitting unit and the signal detecting unit when the right wearing unit is on a right side of the left wearing unit.

7. The foot wearing device according to claim 6, wherein the shielding unit is arranged at a right side of the left wearing unit and/or a left side of the right wearing unit.

8. The foot wearing device according to claim 1, wherein a signal transmitting angle along which the signal transmitting unit transmits signals is 120 degrees to 180 degrees.

9. The foot wearing device according to claim 1, wherein the signal transmitting unit is a photoelectric signal transmitter, and the signal detecting unit is a photoelectric signal detector.

10. The foot wearing device according to claim 1, wherein the prompt unit is one or more of a buzzer, a horn, a light prompt, a vibration device, and a graphene heating device.

11. The foot wearing device according to claim 1, further comprising a power unit, wherein the power unit comprises a left power part arranged at the left wearing unit and a right power part arranged at the right wearing unit.

12. The foot wearing device according to claim 11, wherein each of the left power part and the right power part is a chargeable battery.

13. A method for correcting sitting posture, comprising:
provide a foot wearing device, wherein the foot wearing device comprises:
left wearing unit, configured to be worn on a left foot of a user;
a right wearing unit, configured to be worn on a right foot of the user;
a signal transmitting unit, arranged on one of a left side of the left wearing unit and a right side of the right wearing unit and configured to transmit signals;
a signal detecting unit, arranged on the other of the left side of the left wearing unit and the right side of the right wearing unit and configured to detect signals transmitted by the signal transmitting unit; and
a prompt unit, electrically connected to the signal detecting unit and configured to prompt the user if the signal detecting unit detects that there are signals transmitted by the signal transmitting unit;
wear the left wearing unit on a user's left foot and wear the right wearing unit on the user's right foot;
detect by the signal detecting unit whether there are signals transmitted by the signal transmitting unit;
prompt the user by the prompt unit to correct sitting posture if there are signals transmitted by the signal transmitting unit.

14. The method according to claim 13, wherein the foot wearing device further comprises a first timing switch connected between the signal detecting unit and the prompt unit, the method further comprises:
time by the first timing switch a time interval t1 between two adjacent times when the signal detecting unit detects signals transmitted by the signal transmitting unit;
switch on a connection between the signal detecting unit and the prompt unit if the time interval t1 is less than a predetermined value T1; and
switch off the connection between the signal detecting unit and the prompt unit if the time interval t1 is not less than a predetermined value T1.

15. The method according to claim 13, wherein the foot wearing device further comprises a second timing switch connected between the signal detecting unit and the prompt unit, the method further comprises:
time by the second timing switch a signal duration t2 when the signal detecting unit detects signals transmitted by the signal transmitting unit;
switch on a connection between the signal detecting unit and the prompt unit if the signal duration t2 is greater than a predetermined value T2;
prompt the user by the prompt unit to correct sitting posture; and
switch off the connection between the signal detecting unit and the prompt unit if the signal duration t2 is not greater than a predetermined value T2.

16. The method according to claim 13, wherein the foot wearing device further comprises a first timing switch connected between the signal detecting unit and the prompt unit and a second timing switch connected between the signal detecting unit and the prompt unit, the method further comprises:
time by the first timing switch a time interval t1 between two adjacent times when the signal detecting unit detects signals transmitted by the signal transmitting unit;
switch on a connection between the signal detecting unit and the prompt unit if the time interval t1 is less than a predetermined value T1;
prompt the user by the prompt unit to correct sitting posture; and
time by the second timing switch a signal duration t2 when the signal detecting unit detects signals transmitted by the signal transmitting unit, if the time interval t1 is not less than a predetermined value T1;
switch on a connection between the signal detecting unit and the prompt unit if the signal duration t2 is greater than a predetermined value T2;
prompt the user by the prompt unit to correct sitting posture; and
switch off the connection between the signal detecting unit and the prompt unit if the signal duration t2 is not greater than a predetermined value T2.

17. The foot wearing device according to claim 16, wherein after the step of prompt the user by the prompt unit to correct sitting posture, the method further comprises;
detect by the detecting unit whether there are signals transmitted by the signal transmitting unit; and
prompt the user by the prompt unit to correct sitting posture if there are signals transmitted by the signal transmitting unit.

* * * * *